US010072310B2

(12) United States Patent
Ling

(10) Patent No.: US 10,072,310 B2
(45) Date of Patent: Sep. 11, 2018

(54) PROCESS OF PREPARING FERMENTED MILK BEVERAGE KEEPING HIGH VIABLE CELL COUNT AT AMBIENT TEMPERATURE

(75) Inventor: Haibo Ling, Beijing (CN)

(73) Assignee: BEIJING YIHEOUN TECH. CO., LTD., Beijing (CN)

( * ) Notice: Subject to any disclaimer, the term of this patent is extended or adjusted under 35 U.S.C. 154(b) by 844 days.

(21) Appl. No.: 12/564,762

(22) Filed: Sep. 22, 2009

(65) Prior Publication Data

US 2010/0009034 A1 Jan. 14, 2010

Related U.S. Application Data

(63) Continuation-in-part of application No. PCT/CN2007/002037, filed on Jun. 29, 2007.

(30) Foreign Application Priority Data

Mar. 28, 2007 (CN) .......................... 2007 1 0064896

(51) Int. Cl.
*C12R 1/225* (2006.01)
*A23C 9/123* (2006.01)

(52) U.S. Cl.
CPC ............ *C12R 1/225* (2013.01); *A23C 9/1234* (2013.01); *A23Y 2220/73* (2013.01)

(58) Field of Classification Search
USPC .......................................................... 426/43
See application file for complete search history.

(56) References Cited

U.S. PATENT DOCUMENTS

| | | | |
|---|---|---|---|
| 3,950,544 A * | 4/1976 | Fridman .......................... 426/46 |
| 4,748,025 A * | 5/1988 | Bachmann et al. ............ 426/583 |
| 4,839,281 A | 6/1989 | Gorbach et al. | |
| 5,032,399 A | 7/1991 | Gorbach et al. | |
| 5,413,785 A | 5/1995 | Nanji | |
| 5,709,857 A * | 1/1998 | Morelli et al. ............. 424/93.45 |
| 6,007,808 A * | 12/1999 | De Haen et al. ............. 424/93.4 |
| 6,156,320 A * | 12/2000 | Izvekova et al. ......... 424/197.11 |
| 6,358,521 B1 * | 3/2002 | Izvekova et al. ........... 424/93.45 |
| 6,506,380 B1 * | 1/2003 | Isolauri et al. ............. 424/93.45 |
| 6,596,530 B1 * | 7/2003 | Kimura et al. ............. 435/252.9 |
| 6,835,376 B1 * | 12/2004 | Neeser et al. ............. 424/93.45 |
| 6,872,565 B2 * | 3/2005 | Mollstam et al. ......... 435/252.9 |
| 6,926,891 B1 * | 8/2005 | Neeser et al. ............... 424/93.4 |
| 6,942,849 B2 * | 9/2005 | Neeser et al. .................. 424/50 |
| 7,029,669 B1 * | 4/2006 | Reniero et al. ............. 424/93.45 |
| 7,101,565 B2 * | 9/2006 | Monte .......................... 424/423 |
| 7,112,322 B2 * | 9/2006 | Isolauri et al. ............. 424/93.45 |
| 2002/0028269 A1 * | 3/2002 | Verrips ........................... 426/71 |
| 2003/0113340 A1 * | 6/2003 | Isolauri et al. ............. 424/184.1 |
| 2003/0147857 A1 * | 8/2003 | Monte .......................... 424/93.4 |
| 2003/0161820 A1 * | 8/2003 | Kimura et al. ............. 424/93.45 |
| 2004/0067573 A1 * | 4/2004 | Connolly et al. .......... 435/252.1 |
| 2004/0115773 A1 * | 6/2004 | Arigoni et al. ............. 435/69.2 |
| 2005/0002874 A1 * | 1/2005 | Mollstam et al. ............. 424/48 |
| 2005/0158254 A1 * | 7/2005 | Mollstam et al. ............. 424/50 |
| 2006/0013806 A1 * | 1/2006 | Isolauri et al. ............ 424/93.45 |
| 2006/0165661 A1 * | 7/2006 | Speelmans et al. ......... 424/93.4 |
| 2007/0110849 A1 * | 5/2007 | Secretin .......................... 426/72 |
| 2007/0123460 A1 * | 5/2007 | Chang et al. .................... 514/12 |
| 2007/0269515 A1 * | 11/2007 | Henriksen et al. ........... 424/480 |
| 2008/0095752 A1 * | 4/2008 | Chiang et al. ............. 424/93.45 |
| 2009/0274661 A1 * | 11/2009 | Mercenier et al. .......... 424/93.4 |
| 2011/0020304 A1 * | 1/2011 | Sprenger .................... 424/93.45 |

FOREIGN PATENT DOCUMENTS

| | | |
|---|---|---|
| CN | 1187772 A | 7/1998 |
| CN | 1487798 A | 4/2004 |
| JP | 2007-28920 | 2/2007 |
| WO | WO 01/88510 | * 11/2001 ............. C12N 15/56 |

OTHER PUBLICATIONS

Sodini et al., Effect of Milk Base and Starter Culture on Acidification, Texture, and Probiotic Cell Counts in Fermented Cell Counts in Fermented Milk Processing, J. Dairy Sci. 85:2479-2488 (Sodini).*
Grosso et al., Stability of Free and Immobilized Lactobacillus Acidophilus and Bifidobacterium Lactis in Acidified Milk and of Immobilized B. Lactis in Yoghurt, Brazilian Journal of Microbiology (2004) 35:151-156.*
Schkoda, P. Influence of the protein content on structural characteristics of stirred fermented milk, Milchwissenschaft [Milchwissenschaft]. vol. 56, No. 1, pp. 19-22. 2001 (abstract).*
Ding et al., Acid, Bile, and Heat Tolerance of Free and Microencapsulated Probiotic Bacteria, Journal of Food Science, vol. 72, nr 9, 2007.*
Farnworth et al., Growth of Probiotic Bacteria and Bifidobacteria in a Soy Yogurt Formulation, International Journal of Food Microbiology, 11, 174-181, 2007.*
Ying1, etal., Beneficial functions of probiotics LGG and application in dairy products-- (Food Science and Technology) 2006.*
Visconti, et al., Study of Adhesion and Survival of Lactobacilli and Bifidobacteria on Table Olives with the Aim of Formulating a New Probiotic Food, Applied and Environamnetla Microbiology, vol. 71, No. 8, Aug. 2005, p. 4233-4240.*

(Continued)

*Primary Examiner* — D Lawrence Tarazano
*Assistant Examiner* — Philip Dubois
(74) *Attorney, Agent, or Firm* — Michael Ye; Morris, Manning & Martin, LLP

(57) ABSTRACT

The invention provides a process of preparing fermented milk beverage keeping high viable cell count at ambient temperature. The process includes the steps of adding regular yoghurt *lactobacillus* into milk for fermentation, fermenting until pH value to 3.8-4.8, diluting, mixing and sterilizing with conventional method, adding concentrated culture, concentrated frozen culture or freeze dried culture containing *Lactobacillus rhamnosus* ATCC 53103 into mixed milk beverage at aseptic condition. According to various pH value of finished product, it can be stored at ambient temperature for 1-6 months, and the viable cell count will not be less than $10^5$ cfu/ml milk beverage. The indexes of storage period and viable cell count are much higher than fermented milk beverage produced by conventional process. Thereby the defect that fermented milk beverage has short shelf life and low viable cell count at ambient temperature is overcome efficiently.

11 Claims, No Drawings

(56) References Cited

OTHER PUBLICATIONS

Analie Lourens-Hattingh et al., "Yogurt as probiotic carrier food" International Dairy Journal, 2001 Elsevier Science Ltd., vol. 11, pp. 1-17.
N.P. Shah, "Symposium: Probiotic Bacteria: Selective Enumeration and Survival in Dairy Foods" Journal of Dairy Science, 2001, vol. 83, No. 4, pp. 894-907.
Gou Qingquan et al., "The main starter bacteria to Induce the postacidification of yogurt" Food and Machinery, Dec. 2002, vol. 1, No. 87, pp. 14-15.
Saxelin, Maija, "Lactobacillus GG—A Human Probiotic Strain With Thorough Clinical Documentation", Food Rev. Int., 1997, pp. 293-313, vol. 13, No. 2.

\* cited by examiner

PROCESS OF PREPARING FERMENTED MILK BEVERAGE KEEPING HIGH VIABLE CELL COUNT AT AMBIENT TEMPERATURE

CROSS-REFERENCE TO RELATED APPLICATIONS

This application is a continuation-in-part of international application No. PCT/CN2007/002037 filed on Jun. 29, 2007, which claims the priority benefits of China application No. 200710064896.X filed on Mar. 28, 2007. The contents of these prior applications are hereby incorporated by reference in its entirety.

TECHNICAL FIELD

The invention relates to fermented milk field, in particular, a process of preparing fermented milk beverage keeping high viable cell count at ambient temperature.

TECHNICAL BACKGROUND

Fermented milk, especially yoghurt, is a fermented milk product highly appreciated by consumers. The reason of being welcomed owes to that it comprises viable *lactobacillus* which are helpful to human health. It is generally recognized that per ml (or g) of product should comprise at least $10^5$-$10^7$ cfu of viable *lactobacillus*, and at least 100 ml (or g) of product should be consumed every day so as to be helpful to human health. Therefore, it is very important to keep this *lactobacillus* viable in the fermented products before consumption.

However, under the conditions that cold chain is not perfect and the products are stored without refrigeration for relatively long time, the viability of *lactobacillus* in fermented milk is usually very low, even no viable bacteria can be detected (W. T. Hamann and E. H. Marth, *Survival of Streptococcus thermophilus and Lactobacillus bulgaricus in commercial and experimental yoghurts*, J. Food Protection, 47:781-786, 1984). The reason for this phenomenon is that storage under non-cold chain conditions leads to serious post acidification of yoghurt products, and over post acidification can speed up the death of *lactobacillus*. This point has been illustrated sufficiently in previous research reports (GUO, Qinquan and ZHANG, Lanwei, The main starter bacteria to induce the post acidification of yoghurt and the characteristics thereof, FOOD AND MACHINERY, 87 (1):14-16, 2002; W. T. Hamann and E. H. Marth, J. Food Protection, 47:781-786, 1984). Many developing countries lack perfect cold chain system, so fermented milk is often transported, stored and sold in a non-refrigeration state, which leads to degradation of product's quality and great shortening of product's shelf life.

Some documents have reported processes for increasing the cell count of viable *lactobacillus*. These processes include: adding antioxidant (such as VC), adding prebiotics (such as oligosaccharides), encapsulating *lactobacillus* into microcapsule, non-adding *Lactobacillus bulgaricus* and decreasing oxidation-reduction potential (such as adding cysteine) etc. . . . (N P. Shah, *Probiotic bacteria: Selective enumeration and survival in dairy foods*, J. Dairy Sci., 83: 894-907, 2000; A. Lourens and B. C. Viljoen, *Int. Dairy J.*, 11: 1-17, 2001). However, the effect of these processes is rather limited.

The root cause of the problem lies in that most of *lactobacillus* can use lactose for fermentation, and lactose fermentation will produce lactic acid, thereby decrease the pH value of milk quickly, which directly leads to the decreasing of the cell count of *lactobacillus*. For example, when *Streptococcus thermophilus* and/or *Lactobacillus bulgaricus* are used as fermentation strains and the milk is fermented at about 43° C., big quantity of lactic acid will be produced in 2-5 hours, which makes the pH value of milk decrease quickly to below 4.5 and leads to the degradation of viability or death of *lactobacillus*.

Thus, controlling acid production of fermented milk is the key to solve the problem that store fermented milk at ambient temperature with high viable cell count.

*Lactobacillus rhamnosus* (available from American Type Culture Collection, bacterial strain number: ATCC 53103) is a probiotic strain isolated from healthy human body (U.S. Pat. No. 4,839,281; U.S. Pat. No. 5,032,399), and it can get rid of endotoxin from blood plasma (U.S. Pat. No. 5,413, 785). The distinctive characteristic of this bacterium is that it does not ferment lactose and is resistant to acid and oxygen. Since this bacterium has the function of prevention and treatment of stomach upset (such as diarrhea) and improvement of immunity, it is used in healthy and functional products (such as yoghourt). The details of the biological characteristics and probiotic functions of this bacterium, please refer to above-mentioned patents and the review article—M. Saxelin, *Lactobacillus GG A human probiotic strain with thorough clinical documentation*, Food Rev. Int., 13: 293-313, 1997.

SUMMARY OF INVENTION

1. Technical Problem to Be Solved

One aspect of the invention is to provide a process of preparing fermented milk beverage keeping high viable cell count at ambient temperature.

2. Technical Solutions

Based on the invention, related technical terms are defined as follows.

Post acidification: after the fermentation process of yoghourt or fermented milk stops, the *lactobacillus* in the yoghourt continues to produce acid, thereby leading to a higher acidification of the product, which is also called post production acidification or post fermentation acidification.

The term "ambient temperature" herein refers to a temperature which can be reached indoor under normal conditions, such as 0-40° C., preferably 10-30° C.

The process according to an embodiment of the invention includes: firstly using regular yoghourt *lactobacillus* (consisting of single or mixing strain of *Lactobacillus bulgaricus* and/or *Streptococcus thermophilus*) for fermentation, after diluting, mixing and sterilizing, adding *Lactobacillus rhamnosus* ATCC 53103 (American Type Culture Collection, Manassas, Va., Catalog No. 53103) under aseptic condition, which uses limited monosaccharides (produced by fermentation of regular yoghourt *lactobacillus*) for proliferation and produces lactic acid, the pH value of the product can be decreased to certain value and be stable comparatively during storage.

The process according to an embodiment of the invention, means that firstly adding regular yoghurt *lactobacillus* into milk for fermentation, fermenting until pH value to 3.8-4.8, adding some sweeters, flavorings, thickening, emulsifying stabilizers and water, mixing diluting, and sterilizing, then adding concentrated liquid culture, concentrated frozen culture or freeze dried culture containing *Lactobacillus rham-*

*nosus* ATCC 53103 (available from American Type Culture Collection) to the mixed milk beverage under aseptic condition.

According to the process of an embodiment of the invention, the pH value of mixing milk beverage is set based on the pH value decrease that can be induced by the quantity of monosaccharide contained in the fermentation liquid. For example, if the quantity of monosaccharide contained in the fermentation liquid can lead to a pH value decrease of 0.2 and the pH value of finished product of mixed milk needs to be 4.2, then setting the pH value of mixing at 4.4, since *Lactobacillus rhamnosus* ATCC 53103 will gradually produce acid in mixed milk beverage until the monosaccharide in the mixed milk beverage is consumed, then the pH value will be stabilized at the setting value of finished product.

Wherein, said milk beverage is made from fresh milk or reconstituted milk (includes but not limited to fresh milk or reconstituted milk of cow milk or goat milk) or fresh milk or reconstituted milk into which concentrated whey protein is added. The protein concentration of the milk beverage is 0.1-5%. Preferably, the protein concentration of the milk beverage is 0.7-2.5%.

In the process according to an embodiment of of the invention, the yoghourt *lactobacillus* can be any bacteria for preparing yoghourt which are known to people skilled in the art. *Lactobacillus bulgaricus* and/or *Streptococcus thermophilus* are preferred, and the addition amount can be $10^3$-$10^8$ cfu/ml milk.

The fermentation temperature of regular yoghourt is 35-45° C., and the fermentation time is 2.5-10 hours.

Said diluting and mixing means using fermented milk as base, adding some sweeteners, acidulants, flavorings, thickening and emulsifying stabilizers, and water, mixing and diluting the fermented milk with 1.5-10 times, to make the beverage containing 0.3-2.5% milk protein.

In the invention, the addition amount of *Lactobacillus rhamnosus* ATCC 53103 is not limited theoretically. According to the principle of economy and effectiveness, the addition amount of *Lactobacillus rhamnosus* ATCC 53103 is preferably $10^3$-$10^8$ cfu/ml milk beverage, more preferably $10^5$-$10^7$ cfu/ml milk beverage.

*Lactobacillus rhamnosus* ATCC 53103 will gradually produce acid in the mixed milk beverage, until the monosaccharides inside are consumed, and the variation range of pH value is within 0.1-1.0 during the shelf life.

3. Advantageous Effects

The fermented milk beverage prepared by the process according to an embodiment of the invention can be stored for 1-6 months under ambient temperature (10-30° C.) and keep viable cell count at least $10^5$ cfu/ml milk beverage. The indexes of storage period and viable cell count are much higher than fermented milk beverage produced by conventional process. Thereby the defect that fermented milk beverage has short shelf life and low viable cell count at ambient temperature is overcome.

DESCRIPTION OF EMBODIMENTS

The following examples are used to illustrate the invention, but not to limit the scope of the invention.

Example 1 Fermented Milk Beverage Prepared with the Addition of *Lactobacillus rhamnosus* after Regular Yoghurt *Lactobacillus* Fermentation and Sterilization and its Storage Test Add 8% whole milk powder and 3% concentrated whey protein (WPC-80, protein content 80%) into water, thereby obtain reconstituted whole milk. Take 1000 ml reconstituted whole milk and heat at 115° C. for 15 minutes, then cool down. Inoculate with regular yoghurt bacteria BF-203 (available from BEIING FUMENGTE BIOTECHNOLOGY COMPANY LTD, composed of *Streptococcus thermophilus* and *Lactobacillus bulgaricus*), ferment until pH value to 4.5, cool down to below 25° C.

Use 400 ml of water at 70° C. to dissolve acidic milk beverage stabilizer SY-806 (available from BEIING FUMENGTE BIOTECHNOLOGY COMPANY LTD.) 6 g and Ace-K (available from ZHANGJIAGANG HAOBO CHEMISTRY COMPANY) 0.5 g, stir for 20 minutes and cool down to below 25° C. After hydration for 30 minutes, take 100 ml above-mentioned reconstituted fermented milk into above-mentioned stabilizer solution, adjust pH value of the mixture solution to 4.4 with 10% citric acid, fix the volume with water to 1000 ml, and stir for 5 minutes. Preheat to 70° C., homogenize with the pressure of 20 MPa, then sterilize it at 115° C. for 15 minutes.

Cool it down again to below 37° C., inoculate above-mentioned milk beverage with freeze dried culture powder of *Lactobacillus rhamnosus* ATCC 53103 with the quantity of $5 \times 10^5$ cfu/ml milk beverage. Store the said beverage at 12-25° C. and measure the pH value and viable cell count at different storage period. The results are listed in table 1. The results show that after storage at 12-25° C. for 8 weeks, viable cell count is at least $10^6$ cfu/ml milk beverage, and the pH value of product is above 3.7.

TABLE 1

Viability of *lactobacillus* and the pH value variation of the milk beverage at different storage period

| storage time (week) | pH value | Viable cell count($10^7$ cfu/ml milk beverage) |
|---|---|---|
| 0 | 4.4 | 0.05 |
| 1 | 3.85 | 22 |
| 2 | 3.76 | 27 |
| 3 | 3.72 | 15 |
| 4 | 3.75 | 11 |
| 5 | 3.70 | 8.2 |
| 6 | 3.73 | 7.6 |
| 7 | 3.73 | 3.5 |
| 8 | 3.79 | 0.9 |

Example 2 Fermented Milk Beverage Prepared with the Addition of *Lactobacillus rhamnosus* after Regular Yoghurt *Lactobacillus* Fermentation and Sterilization and its Storage Test According to the same process of Example 1, 14% whole milk powder is used to prepare reconstituted whole milk. Inoculate with regular yoghurt *lactobacillus* BF-306 (available from BEIING FUMENGTE BIOTECHNOLOGY COMPANY LTD, composed of *Streptococcus thermophilus* and *Lactobacillus bulgaricus*), ferment until pH value to 3.8.

Dilute above-mentioned reconstituted fermented milk for 5 times, prepare a milk beverage with 0.7% protein concentration. Adjust pH value of the mixture solution to 4.4 with 10% citric acid. According to the process of Example 1, homogenize and sterilize, then inoculate above-mentioned milk beverage with concentrated culture of *Lactobacillus rhamnosus* ATCC 53103 with quantity of $1.5 \times 10^7$ cfu/ml milk beverage. Store the said beverage at 12-25° C. and measure the pH value and viable cell count at different period. The results are listed in table 2. The results show that after storage at 12-25° C. for 6 months, viable cell count of *Lactobacillus rhamnosus* is at least $10^7$ cfu/ml milk beverage, and the pH value of product is above 4.2.

TABLE 2

Viability of *lactobacillus* and the pH value variation of the milk beverage at different storage period

| storage time (month) | pH value | Viable cell count($10^7$ cfu/ml milk beverage) |
|---|---|---|
| 0 | 4.4 | 1.5 |
| 1 | 4.17 | 28 |
| 2 | 4.20 | 32 |
| 3 | 4.19 | 25 |
| 4 | 4.23 | 7.1 |
| 5 | 4.25 | 6.5 |
| 6 | 4.30 | 2.4 |

Example 3 Fermented Milk Beverage Prepared with the Addition of *Lactobacillus rhamnosus* after Regular Yoghurt *Lactobacillus* Fermentation and Sterilization and its Storage Test According to the same process of Example 1, adding 3.5% whole milk powder into fresh milk containing 11.5% milk solid to prepare whole milk with 15% solid concentration. Inoculate with regular yoghurt *lactobacillus* BF-301 (available from BEIING FUMENGTE BIOTECHNOLOGY COMPANY LTD, composed of *Streptococcus thermophilus* and *Lactobacillus bulgaricus*), ferment until pH value to 4.0.

Dilute above mentioned reconstituted fermented milk for 5.5 times, prepare a milk beverage with 0.7% protein concentration. Adjust pH value of the mixture solution to 4.3 with 10% citric acid. According to the process of Example 1, homogenize, mix and sterilize, then inoculate above-mentioned milk beverage with *Lactobacillus rhamnosus* ATCC 53103 with quantity of $2\times10^6$ cfu/ml milk beverage. Store the said beverage at 37° C. for 15 days and measure the pH value and viable cell count. The results are listed in table 3. The results show that after storage at 37° C. for 15 days, viable cell count is at least $10^7$ cfu/ml milk beverage, and the pH value of product is above 3.9.

TABLE 3

Viability of *lactobacillus* and pH value variation of the milk beverage stored at 37° C. for 15 days

| storage time (day) | pH value | Viable cell count($10^7$ cfu/ml milk beverage) |
|---|---|---|
| 0 | 4.31 | 0.15 |
| 1 | 4.17 | 26 |
| 4 | 3.94 | 17 |
| 7 | 3.98 | 21 |
| 10 | 3.93 | 3 |
| 15 | 3.93 | 1.1 |

Example 4 Fermented Milk Beverage Prepared with the Addition of *Lactobacillus rhamnosus* after Regular Yoghurt *Lactobacillus* Fermentation and Sterilization and its Storage Test According to the same process of Example 1, 15% whole milk powder is used to prepare reconstituted whole milk. Inoculate with regular yoghurt *lactobacillus* BF-208 (available from BEIING FUMENGTE BIOTECHNOLOGY COMPANY LTD, composed of *Streptococcus thermophilus*), ferment until the pH value to 4.5.

For preparing a milk beverage with 1.8% protein in finished product, dilute above-mentioned reconstituted fermented milk for 2 times. Mix and sterilize, then inoculae above-mentioned milk beverage with *Lactobacillus rhamnosus* ATCC 53103 with quantity of $5\times10^6$ cfu/ml milk beverage. Store the said beverage at 12-25° C. and measure the pH value and viable cell count at different period. The results are listed in table 4. The results show that after storage at 12-25° C. for 6 months, viable cell count is at least $10^7$ cfu/ml milk beverage, and the pH value of product is above 4.3.

TABLE 4

Viability of *lactobacillus* and the pH value variation of the milk beverage at different storage period

| storage time (month) | pH value | Viable cell count($10^7$ cfu/ml milk beverage) |
|---|---|---|
| 0 | 4.5 | 0.5 |
| 1 | 4.33 | 27 |
| 2 | 4.35 | 29 |
| 3 | 4.40 | 32 |
| 4 | 4.37 | 22 |
| 5 | 4.41 | 15 |
| 6 | 4.33 | 7.6 |

I claim:

1. A process of preparing fermented milk beverage keeping high viable cell count at ambient temperature, comprising:
    adding regular yoghurt *lactobacillus* into milk for fermentation;
    fermenting said milk until pH value to 3.8-4.8;
    diluting and mixing the fermented milk with additives and water;
    sterilizing the diluted and mixed fermented milk; and
    adding *Lactobacillus rhamnosus* ATCC 53103 into the sterilized fermented milk beverage at aseptic condition to produce a final product,
    wherein said regular yoghurt *lactobacillus* is selected from the group consisting of a single strain of *Lactobacillus bulgaricus*, a single strain of *Streptococcus thermophilus*, mixed strains of *Lactobacillus bulgaricus*, mixed strains of *Streptococcus thermophilus*, and mixed strains of *Lactobacillus bulgaricus* and *Streptococcus thermophilus*, and
    wherein said final product can be stored for 1-6 months under room temperature with a viable cell count of *Lactobacillus rhamnosus* ATCC 53103 of at least $10^5$ cfu/ml milk beverage.

2. The process according to claim 1, wherein said milk beverage is made from fresh milk or reconstituted milk, or fresh milk or reconstituted milk into which concentrated whey protein is added, the protein concentration of the milk beverage is 0.1-5%.

3. The process according to claim 2, wherein the protein concentration of the milk beverage is 0.3-2.5%.

4. The process according to claim 2, wherein said *Lactobacillus rhamnosus* ATCC 53103 is added in the form of concentrated liquid culture, concentrated frozen culture or freeze-dried culture.

5. The process according to claim 1, wherein the fermentation temperature of regular yoghurt *lactobacillus* is 35-45° C., and the fermentation time is 2.5-10 hours.

6. The process according to claim 1, wherein said diluting and mixing means the fermented milk is mixed to prepare milk beverages containing 0.7-2.5% milk protein, and the fermented milk is diluted to 1.5-10 times.

7. The process according to claim 1, wherein the pH value of finished product of said mixed milk beverage is finally controlled within the range of 3.5-4.7.

8. The process according to claim 7, wherein said *Lactobacillus rhamnosus* ATCC 53103 is added in the form of concentrated liquid culture, concentrated frozen culture or freeze-dried culture.

9. The process according to claim 1, wherein the addition amount of said *Lactobacillus rhamnosus* ATCC 53103 is $10^5$-$10^7$ cfu/ml milk beverage.

10. The process according to claim 1, wherein said *Lactobacillus rhamnosus* ATCC 53103 is added in the form of concentrated liquid culture, concentrated frozen culture or freeze-dried culture.

11. A fermented milk beverage prepared by a process comprising the steps of:

adding regular yoghurt *lactobacillus* into milk for fermentation;

fermenting said milk until pH value to 3.8-4.8;

diluting and mixing the fermented milk with additives and water;

sterilizing the diluted and mixed fermented milk; and adding *Lactobacillus rhamnosus* ATCC 53103 into the sterilized fermented milk beverage at aseptic condition to produce a final product, wherein said regular yoghurt *lactobacillus* is selected from the group consisting of a single strain of *Lactobacillus bulgaricus*, a single strain of *Streptococcus thermophilus*, mixed strains of *Lactobacillus bulgaricus*, mixed strains of *Streptococcus thermophilus*, and mixed strains of *Lactobacillus bulgaricus* and *Streptococcus thermophilus*, and wherein said final product keeps a viable cell count of *Lactobacillus rhamnosus* ATCC 53103 of at least $10^5$ cfu/ml milk beverage for 1-6 months when stored at room temperature.

* * * * *